United States Patent [19]

Gralnick

[11] Patent Number: 5,231,025
[45] Date of Patent: Jul. 27, 1993

[54] ANTI-PLATELET MONOCLONAL ANTIBODY

[75] Inventor: Harvey R. Gralnick, Kensington, Md.

[73] Assignee: The United States of America as represented by the Department of Health and Human Services, Washington, D.C.

[21] Appl. No.: 432,126

[22] Filed: Nov. 3, 1989

[51] Int. Cl.⁵ .................. C12N 5/12; C07K 15/28
[52] U.S. Cl. .................. 435/240.27; 530/388.1; 530/388.25
[58] Field of Search .............. 530/387, 530/413, 415, 388.1, 388.25; 435/240.27, 172.2, 70.21; 935/104; 424/85.8

[56] References Cited

PUBLICATIONS

Sofer, G. et al., Biotechniques, 1983 Nov./Dec. pp. 198–203.
Kambayashi, H. et al., Leucocyte Typing III ed. by A. J. McMichael, p. 787, 1987.

Primary Examiner—David L. Lacey
Assistant Examiner—Susan L. Futrovsky
Attorney, Agent, or Firm—Birch, Stewart, Kolasch & Birch

[57] ABSTRACT

A unique anti-platelet monoclonal antibody which binds to human platelet glycoprotein IV, and various utilities of the monoclonal antibody are described.

4 Claims, 4 Drawing Sheets

200—

116.2—

92.5—

66.2—

45—

ANTI-PLATELET MONOCLONAL ANTIBODY

The present invention is related generally to monoclonal antibodies. More particularly, the present invention is related to a unique monoclonal antibody (Mab) against resting human platelets, said Mab being designated herein as 5G8 and which recognizes a human platelet surface protein of about 88kD, in both reduced and nonreduced state. Such a monoclonal antibody has not heretofore been known or described.

BRIEF DESCRIPTION OF THE DRAWINGS

Various features and attendant advantages of the invention will be better understood upon a reading of the following detailed description when considered in connection with the accompanying drawings wherein:

FIG. 2H–2F shows the dose response curve of the 5G8 antibody added to normal platelet-rich plasma. FIG. 2A platelet-rich plasma without the addition of monoclonal antibody 5G8, FIG. 2B, addition of 1 μg/ml 5G8, FIG. 2C addition of 5 μg/ml, FIG. 2D, addition of 10 μg/ml, FIG. 2E addition of 20 μg/ml, and FIG. 2F addition of 40 μg/ml. Normal platelet-rich plasma by itself did not aggregate; however, after the addition of 185G8 from 1 to 40 micrograms/ml final concentration, the platelet aggregation ensued. There was a clear dose response curve between the amount of 5G8 added and the initial slope and total amount of platelet aggregation.

FIG. 3 demonstrates that the antibody of the present invention increases the binding of fibronectin, fibrinogen, or von Willebrand factor to unstimulated platelets (FIG. 3a). This was related to the amount of antibody present. When the antibody was incubated with the ligand rather than with the platelets, this had no effect on the binding of the ligand to platelets. Lower concentrations of 5G8 can enhance binding of ligands to platelets that have been minimally stimulated. The largest increase in binding was observed with either ADP or epinephrine as agonists and fibrinogen 3b or von Willebrand factor 3c as the ligands. The agonist is 2 μM ADP. The antibody can also enhance the binding of fibrinogen, von Willebrand factor and fibronectin to platelets which had been previously stimulated with thrombin. The greatest enhancement of binding was observed with the agonist ADP and epinephrine. Note that at 0.1 μg/ml 5G8 increases the binding of fibrinogen 12 fold over control (no antibody present) binding, and 5G8 at 0.1 μg/ml increases von Willebrand factor 4 fold over control. In FIG. 3a 0.1 μg/ml has no effect on fibrinogen or von Willebrand factor binding.

DETAILED DESCRIPTION OF THE INVENTION

Figure 1:
FIG. 1 demonstrates the platelet surface glycoprotein which is precipitated by the antibody 5G8 in a 5% polyacrylamide gel in the presence of SDS in a nonreduced state, however identical results were obtained when the antigens were reduced (88kD). Demonstrated in lane 1 is the immunoprecipitate of an antibody against GMP140. In lane 3 is the immunoprecipitate by another antibody 76D which recognizes the Glycoprotein Ia/II complex, molecular weight 150 and 135kD. In lane 2 the results indicate that the 5G8 antibody immunoprecipitates a surface protein that has a molecular weight of 88kD.
Figures 2A, 2B, 2C, 2D, 2E, 2F:
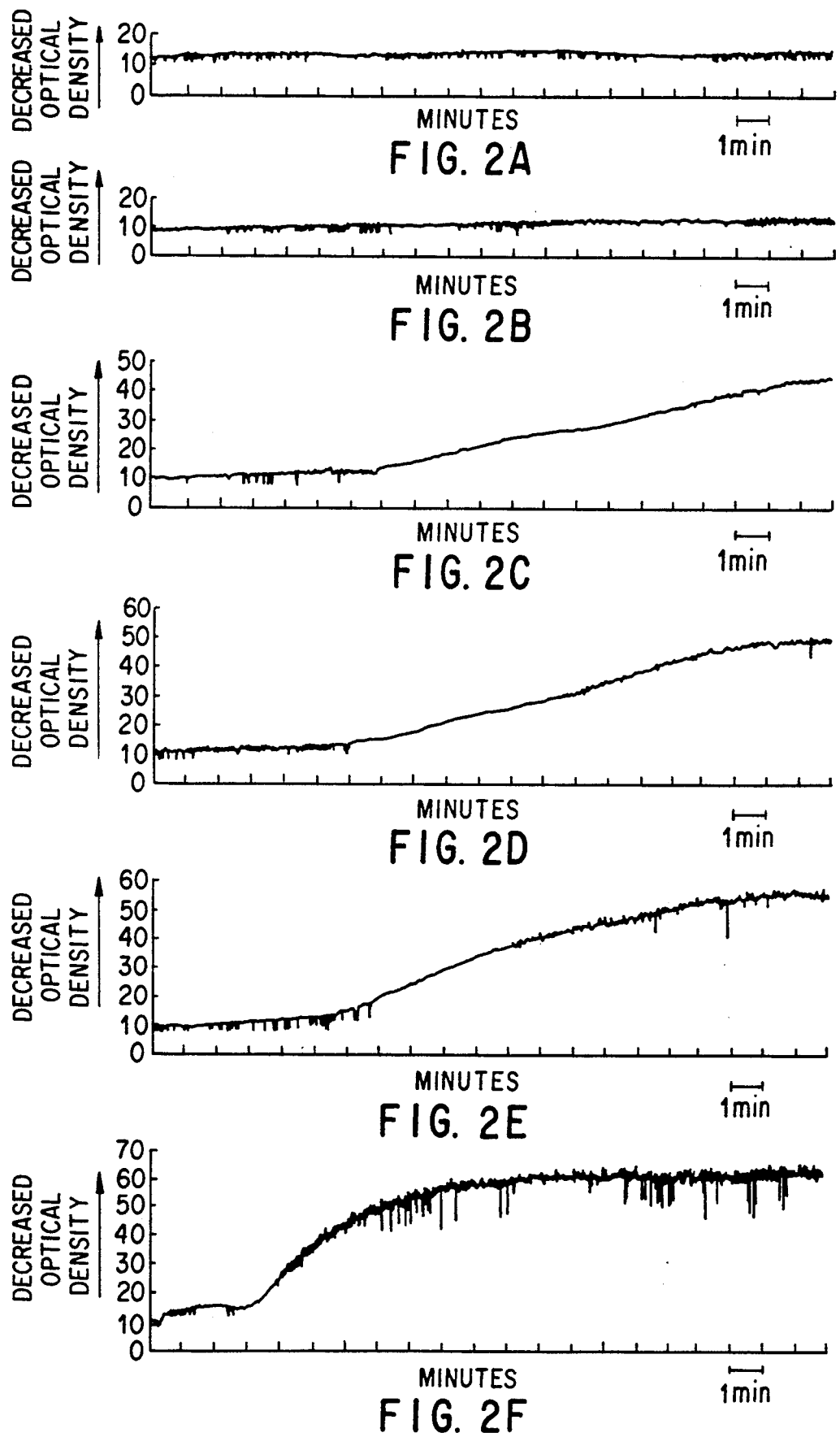

Various objects and advantages of the present invention are achieved by producing monoclonal antibody 5G8 which, inter alia, has the following properties.
(a) Belongs to subclass IgG1.
(b) Binds to about 11,000 sites per platelet with a platelet surface protein of about 88kD in reduced or nonreduced form (FIG. 1).
(c) Induces spontaneous platelet aggregation in the presence of plasma proteins, such as when added to whole blood or to normal platelet rich plasma, causing release of internal platelet organelles and formation of large platelet aggregates (FIG. 2).
(d) Distinctive from other platelet related MAbs, the MAb specifically recognizes glycoprotein IV (GPIV) and modulates platelet aggregation by binding to an epitope on GPIV and does not recognize GP IIb/IIIa complex.
(e) Platelet aggregation induced by this MAb is calcium dependent, but does not require magnesium and is not affected by aspirin treatment of platelets or by released ADP, nor other agonists are required for aggregation reaction to take place.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred materials and methods are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "substantially pure" as used herein means as pure as can be obtained by conventional purification and isolation techniques well known to one of ordinary skill in the art.

MATERIALS AND METHODS

The immunogen used for production of the monoclonal antibody 5G8 was stimulated platelets that had been formalin fixed after 5 minutes incubation with thrombin. Before stimulation and fixation the platelets were purified from other cells and plasma proteins by centrifugation on arabinogalactan gradient (5 ml of 10% and 3 ml of 20%). The platelets were prepared from whole blood by centrifugation at 600 g for 3 minutes at room temperature (about 22°–24° C.). Platelet-rich plasma was removed and was separated from plasma proteins and lymphocytes on an arabinogalactan gradient. These platelets, free of other cellular contamination, were then activated with thrombin 0.1 u/ml, final concentration, per $1 \times 10^8$ platelets. After about 5 minutes, the platelets were mixed with equal volume of 2% formalin. Three injections of these cells were made into BALBc mice prior to the fusion (vide infra). The fusion was performed with PU mouse myeloma cells and murine splenocytes using polyethylene glycol. At 7–10 days, the wells were inspected for growth positivity. Supernatants were screened for antibody production by standard ELISA technique and by cytometry. The positive individual wells selected by the screening procedures were then expanded to 24 macrowell plates containing H-T media and murine spleen feeder cells. When supernatant from the macrowells were tested and found to be positive, these clones were then subjected to limiting dilution studies, the 5G8 underwent 6 limiting dilutions. The fused cells were then injected intraperitoneally in pristine BALB/c mice, and ascites fluid was collected after 2-3 weeks. The antibody was purified by chromatography over a protein-A Sepharose column. The antibody, 5G8, was found to belong to Ig1 class.

FUSION PROCEDURE

1. Seven days before fusion, pass PU mouse myeloma cells at $3.5 \times 10^5$/ml in complete media with 1% 8-azaguanine (10-20 g/ml) total volume 100 ml. On the fifth day after addition of 8-azaguanine, add 100 ml complete media to culture. On the sixth day, centrifuge cells 100 rpm $10^1$, and resuspend in complete media at a concentration of $3.5 \times 10^5$ cells/ml. On the seventh day cells should be in mid log phase $4-6 \times 10^5$/ml. For each fusion, take $3 \times 10^7$ PU cells and wash in RPMI 1640 with glutamine, Penicillin-streptomycin (pen-strep). (Note no FCS at this step). Resuspend in 1 ml RPMI with glutamine, penstrep.
2. Autoclave PEG for 15'. Dilute v/v with RPMI (Glutamine, pen-strep) and add 1 drop sterile 7.5% sodium bicarbonate for each ml of 50% PEG.
3. Remove immunized mouse spleen aseptically and place in small petri dish containing 8 ml RPMI+-glutamine+2X pen-strep. Use small sterile syringe plunger to homogenize spleen. Transfer spleen to 15 ml centrifuge tube and rinse petri with 2 ml RMPI+-glutamine+2X pen-strep. Let spleen settle 1-2' to get rid of large debris. Remove 9.5 ml and add to washed $3 \times 10^7$ PU cells. Spin at 1400 rpm for 10'. Aspirate off as much supernatant as possible. Gently tap test tube over top of test tube rack to spread out cell pellet. Add 1 ml 50% PEG at 37° C. dropwise over one minute to cell pellet. Add 5 ml RPMI (glutamine, pen-strep) over 5 minutes (add 1 ml in drops over 1 minute, then add 4 ml and wait 4 minutes). Fill tube with RPMI (glutamine, pen-strep) a second time and centrifuge 1000 rpm 10'. Resuspend pellet in 100 ml selective cloning media and place in 5 microtiter 96-well flat bottom plates. Cover/wrap with parafilm and plate in 37° C., 7% $CO_2$ incubation.
4. At 7-10 days inspect wells for growth positivity and acidification of media (yellowing of media). When positive, supernatants must be screened for antibody production and/or antibody specificity by standard ELISA protocol.
5. Individual wells selected by screening procedure are then expanded to 24 macrowell plates containing H-T media and murine spleen feeder cells. Ideally, a limiting dilution (LD) is to be carried out immediately at the time of supernatant positivity; however, it can be carried out at the macrowell step. Regardless of procedure followed, the parenteral "clone" should be cryopreserved as soon as possible.
6. For LD, obtain cell count and viability on clone. Also prepare spleen feeder cells (1 spleen for five plates suspended in 10 ml of HT as per step 3). Essentially want 100 hybridoma cells per 96-well plate and approximately $2 \times 10^5$ spleen feeder cells/well. LD should be carried out $\times 3$ to ensure clonal origin of hybridoma. Subclones from each LD and final clones should be cryopreserved.

Complete Media

RPMI 1640: Biofluids Cat. #102
50 ml Fetal calf serum 309 (heat inactivated): Gibco Cat. #240-6309
10 ml L-glutamine: Gibco Cat. #320-5030
0.5 ml Gentamicin: Gibco Cat. #600-5710.

RPMI 1640

Biofluids VCat. #102

10 ml L-glutamine: Gibco Cat. #320-5030
5.0 ml Penicillin-Streptomycin mixture:
  M.A. Bioproducts Cat. #17-6034.

CDME 450 ml DMEM: Biofluids Cat. #104
0.474 ml Penicillin-streptomycin mixture: M.A. Bioproducts Cat. #17-6034
9.47 ml 200 mM L-glutamine: Gibco Cat. #320-5030
59.3 ml FCS (heat inactivated): Gibco Cat. #240-6309
4.74 ml Nonessential amino acids: M.A. Bioproducts Cat. #173-114A
2.84 ml Sodium pyruvate: Gibco Cat. #320-1360
59.3 ml NCTC 109: Gibco Cat. #320-1340.

Selective cloning media 99 ml CDME
1.0 ml HAT (hypoxanthine, aminopterin, thymidine): Hazelton Cat. #59-77076.

PEG 1500 (polyethylene glycol)

M.A. Bioproducts, Cat. #17-7802

HT (Hypoxanthine, Thymidine)

Hazelton Cat. #59-57076

99 ml CDME
1.0 ml HT.

Costar 96-2311 flat-bottom tissue culture plates

Cat. #3596

A deposit of the hybridoma secreting MAb 5G8 has been made at the American Typeculture Collection, 12301 Parklawn Drive, Rockville, Md., 20852, on Oct. 24, 1989, under accession number HB10272. The deposit shall be viably maintained, replacing if it becomes non-viable during the life of the patent, for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

Specificity of 5G8

Figure 3A:
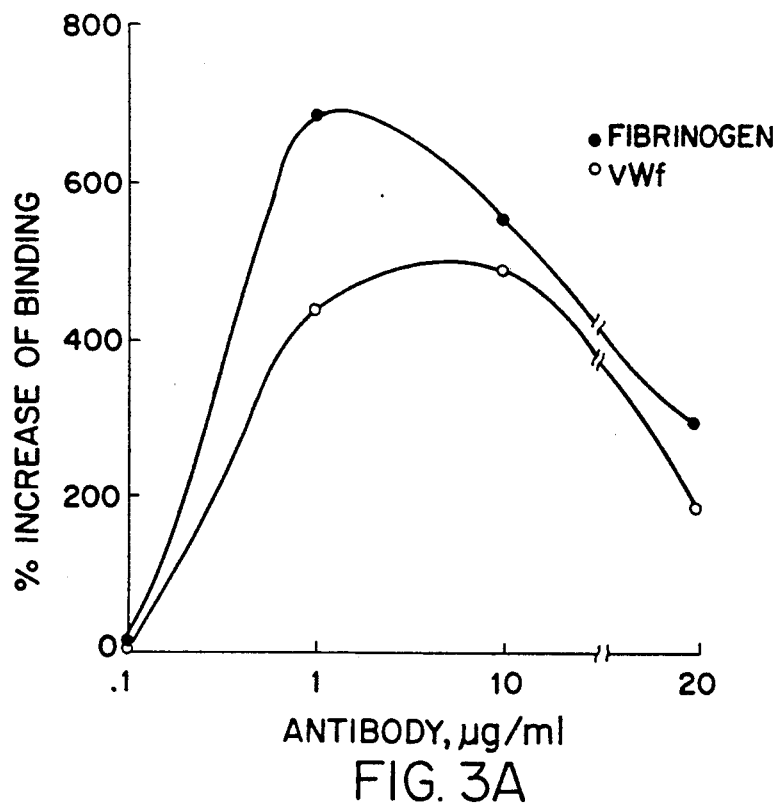
Figure 3B:
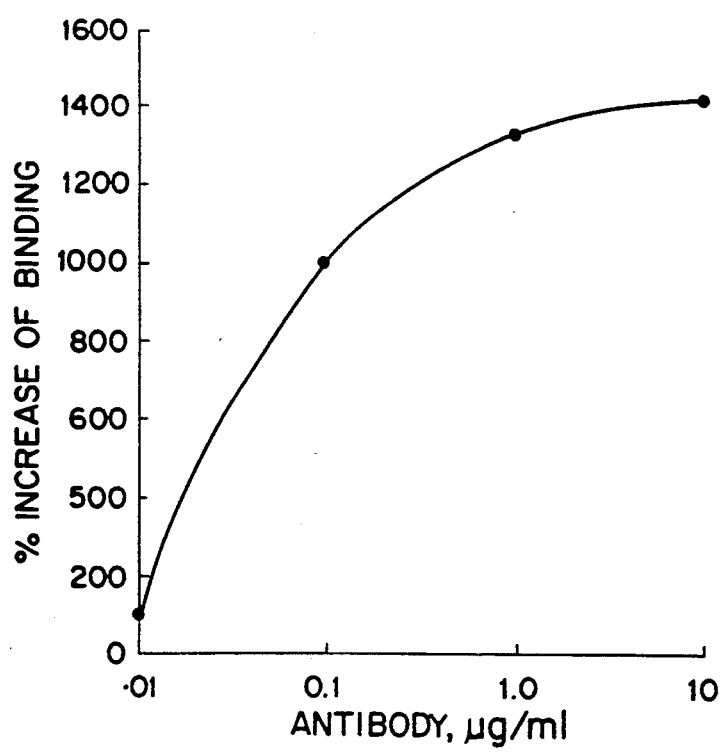
Figure 3C:
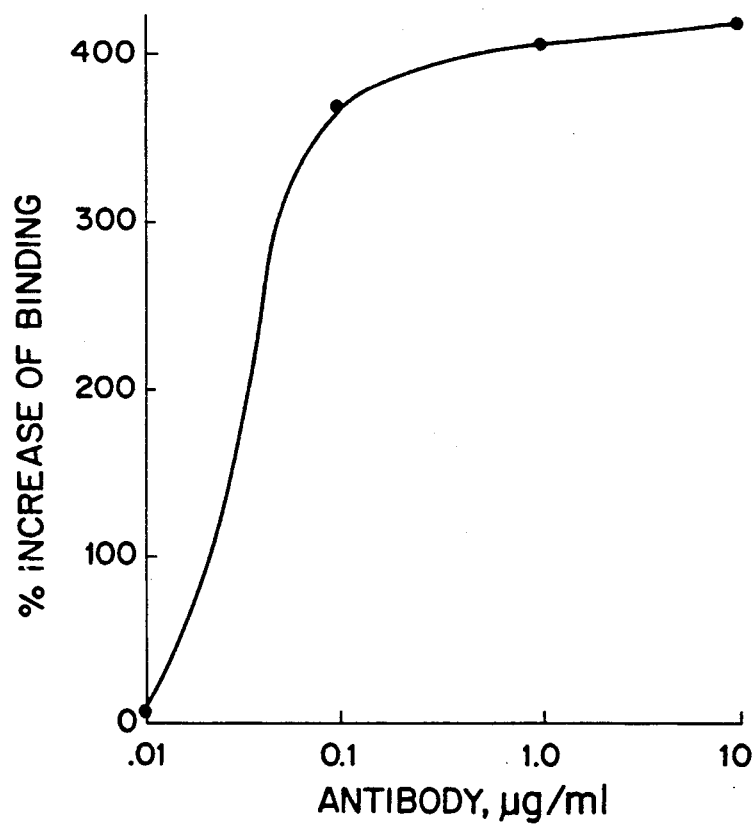

Data presented in FIGS. 1-3 provide evidence of various properties of 5G8 listed herein above.

Utility of 5G8

The application of 5G8 include its utility in identifying a specific platelet defect in individuals with coagulation or hemostatic disorders. This can be done by testing this antibody to see if it enhances platelet aggregation and ligand binding to platelets in certain disease state. This antibody could also be used as an antihemorrhagic agent in which injection of this antibody would enhance platelet attachment and platelet aggregation at sites of vessel wall injury. It would be a useful aid in stopping or reducing surgical bleeding and enhancing normal wound healing. It likewise would be used not only by intravenous injections but could be used topically for a variety of minor cuts, scrapes, bruises, etc., to augment platelet plug formation and blood clotting at that site. A necessity to decrease microvascular bleeding may arise either from surgery or by trauma and 5G8 could be used locally or systemically to augment subnormal or normal mechanisms of hemostasis. It can also be used as a reagent for the purification of GPIV from platelets. This involves the attachment of antibody 5G8 to a semi-solid surface (such as agarose) and to passing normal platelet membranes over this antibody affinity column. The GPIV would be selected (attached) to the antibody and eluted from the antibody. This antibody further allows investigation of the role(s) of GPIV in normal and pathological platelet function. It is not known what pathway(s) of platelet activation and aggregation are involved. New insights into these processes are important in thrombosis and hemostasis.

The availability of the anti-platelet MAb 5G8 also allows the preparation of antihemorrhagic composition containing an effective amount of 5G8 to react with GPIV, and a pharmaceutically acceptable carrier well known to one of ordinary skill in the art, such as physiological saline, nontoxic sterile buffer and the like. A kit comprises a container containing the antibody 5G8, either cryopreserved or otherwise.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. The hybridoma having ATCC deposit number HB10272.

2. The antibody secreted by the hybridoma identified as ATCC HB10272.

3. A monoclonal antibody of claim 2 which specifically binds to platelet glycoprotein IV having the following defining characteristics:
   1) Type IgG, subclass IgG1;
   2) having approximately 11,000 specific binding sites per platelet cell;
   3) specifically binding to a protein expressed on the surface of platelets, said protein having a molecular weight of 88 kilodaltons when determined under either reducing or non-reducing conditions;
   4) specifically binding to platelet glycoprotein IV and not binding to the platelet glycoprotein IIb/IIIa complex;
   5) in the presence of plasma proteins, binding of said monoclonal antibody induces platelet aggregation and causes the release of internal platelet organelles;
   6) causes platelet aggregation in a calcium-dependent, magnesium-independent manner;
   7) causes platelet aggregation independent of aspirin treatment of the platelets;
   8) causes platelet aggregation independent of the presence of adenosine diphosphate or other typical platelet aggregation agonists; and
   9) induces the binding of adhesive proteins, such as fibrinogen and Von Willebrand factor, to the surface of platelets.

4. A composition of matter, comprising an effective amount of the antibody of claim 2 to induce platelet aggregation or to bind with GPIV, and a carrier.

* * * * *